United States Patent
Köhler et al.

(10) Patent No.: US 7,292,717 B2
(45) Date of Patent: Nov. 6, 2007

(54) COMPUTER TOMOGRAPHY METHOD USING REDUNDANT MEASURED VALUES

(75) Inventors: Thomas Köhler, Norderstedt (DE); Roland Proksa, Hamburg (DE)

(73) Assignee: Koninklijke Philips Electronics N.V., Einhoven (NL)

( * ) Notice: Subject to any disclaimer, the term of this patent is extended or adjusted under 35 U.S.C. 154(b) by 212 days.

(21) Appl. No.: 10/560,454

(22) PCT Filed: Jun. 7, 2004

(86) PCT No.: PCT/IB2004/050845

§ 371 (c)(1),
(2), (4) Date: Dec. 14, 2005

(87) PCT Pub. No.: WO2004/111945

PCT Pub. Date: Dec. 23, 2004

(65) Prior Publication Data

US 2006/0159327 A1    Jul. 20, 2006

(30) Foreign Application Priority Data

Jun. 18, 2003  (EP)  .................................. 03101783

(51) Int. Cl.
*G06K 9/00*  (2006.01)
(52) U.S. Cl. ............................ 382/128; 382/131; 378/4
(58) Field of Classification Search ................. 382/128, 382/131; 378/4
See application file for complete search history.

(56) References Cited

U.S. PATENT DOCUMENTS 4,707,822 A * 11/1987 Hopkinson et al. ........... 378/14

(Continued)

FOREIGN PATENT DOCUMENTS

| EP | 0 989 521 A2 | 3/2000 |
|---|---|---|
| WO | WO 98/23209 A1 | 6/1998 |
| WO | WO 98/30980 A1 | 7/1998 |

OTHER PUBLICATIONS

Defrise, M., et al.; Improved 2D rebinning of helical cone-beam CT data using John's equation; 2003; Proc. Of IEEE; pp. 1465-1469.
Lariviere, P., et al.; Transmission Image Reconstruction and Redundant Information in SPECT With Asymmetric Fanbeam Collimation; 2001; Proc. Of IEEE; (15)194-198.

(Continued)

*Primary Examiner*—Bhavesh M Mehta
*Assistant Examiner*—John B Strege

(57) ABSTRACT

The invention relates to a computer tomography method in which a radiation source moves relative to an examination region along, in particular, a helical or circular trajectory. Measured values are acquired by a detector unit and a CT image of the examination region is reconstructed from these measured values. In the reconstruction, a complementary measured value, whose ray is oriented parallel to the ray of the respective measured value that has been acquired but in the opposite direction thereto, is determined for each of at least some measured values that lie within a reconstruction window. Redundant measured values are used to calculate the complementary measured values, with the help in particular of John's equation. The measured values for which complementary measured values have been determined are each replaced by a sum comprised a measured value that has been weighted and a complementary measured value that has been weighted, and a CT image is reconstructed, in particular by an exact method of reconstruction, from the replacement measured values, and where appropriate from acquired measured values, that lie within the reconstruction window.

7 Claims, 9 Drawing Sheets

U.S. PATENT DOCUMENTS

| | | | |
|---|---|---|---|
| 6,072,851 A | 6/2000 | Sivers | 378/15 |
| 6,118,841 A | 9/2000 | Lai | 378/19 |
| 6,233,478 B1 * | 5/2001 | Liu | 600/428 |
| 6,243,437 B1 | 6/2001 | Hu et al. | 378/8 |
| 6,292,526 B1 | 9/2001 | Patch | 378/4 |
| 6,327,326 B1 * | 12/2001 | Flohr et al. | 378/8 |
| 6,829,379 B1 * | 12/2004 | Knoplioch et al. | 382/131 |

OTHER PUBLICATIONS

Katsevich, A. Analysis of an exact inversion algorithm for spiral cone-beam CT; 2002; Phys. Med. Biol., 47:2583-2597.

Kohler, T., et al.; Artifact analysis of approximate helical cone-beam CT reconstruction Algorithms; 2002; Med. Phys.; 29(1):51-64.

Kohler, T., et al.; Evaluation of Helical Cone-Beam CT Reconstruction Algorithms; 2003; Proc. Of IEEE; 1217-1220.

Kohler, T., et al., A fast and efficient method for sequential cone-beam tomography; 2001; Med. Phys.; 28(11)2318-2327.

* cited by examiner

COMPUTER TOMOGRAPHY METHOD USING REDUNDANT MEASURED VALUES

The invention relates to a computer tomography method in which the measured values used to reconstruct a CT image are only ones that lie within a reconstruction window, and it relates in particular to exact computer tomography methods. The invention also relates to a computer tomograph for performing the said method and to a computer program for controlling the computer tomograph.

In known methods of the above-mentioned kind, a radiation source moves along a helical or circular trajectory relative to an examination region in which the object to be examined is situated. As it does so, a detector unit acquires measured values from which a CT image, such as, for example, an image of the distribution of absorption in the examination region, can be reconstructed. Many reconstruction methods, and particularly the exact reconstruction methods, are able to use only a proportion of the measured values. The proportion of the measured values that can be used for reconstruction may for example be defined by a range of solid angles through which the radiation source moves while a point in the examination region that is to be reconstructed is being irradiated, or by a given region on the detector unit. The region in which measured values that are used for reconstruction are situated is called a reconstruction window. Measured values outside the reconstruction window are ignored by methods of the kind mentioned and are termed redundant measured values. A reconstruction method of this kind has been described by, for example, Katsevich in "Analysis of an Exact Inversion Algorithm for Spiral Cone-Beam CT", Physics Medicine and Biology, vol. 47, pp. 2583-2597 (E1). In this case, the radiation source moves along a spiral, i.e. helical, trajectory relative to the examination region and the measured values that are used are only the ones that lie within what is termed the PI window, which will be explained in detail below. Things that are disadvantageous about such methods are that they have a poor signal-to-noise ratio and that, if the object moves, they produce motion artifacts, which are a nuisance.

It is therefore an object of the present invention to specify a computer tomography method of the kind stated in the opening paragraph in which the signal-to-noise ratio is improved and the motion artifacts are reduced.

This object is achieved in accordance with the invention by a computer tomography method having the following steps:

a) generation, by a radiation source, of a conical beam of rays that passes through an examination region and an object situated therein, b) production of a relative movement between the radiation source on the one hand and the examination region on the other hand, which movement comprises at least a rotary movement about an axis of rotation and is in particular in the form of a helix or circle, c) acquisition, by a detector unit and during the relative movement, of measured values that depend on the intensity in the beam of rays on the farther side of the examination region, d) determination, with the help of redundant measured values, of a complementary measured value for each of at least some of the measured values that were acquired in step c) and that lie within a reconstruction window, the rays associated with the given measured value and the complementary measured value belonging to it being oriented in opposite directions to one another, e) replacement of each measured value for which a complementary measured value was determined in step d) by a sum comprising the measured value, having been weighted, and the complementary measured value, having been weighted, f) reconstruction of a CT image of the examination region from the measured values lying within the reconstruction window.

In contrast to known computer tomography methods of the kind defined in the opening paragraph, redundant measured values are used to determine complementary measured values that, when added to their respective associated measured values, replace the latter, which means that redundant measured values too contribute to the reconstruction that follows. The invention is based on the finding that, in computer tomography methods in which the reconstruction is not confined to only a proportion of the measured values, motion artifacts are reduced and the signal-to-noise ratio is improved. Taking account of the redundant measured values therefore results not only in an improvement in the signal-to-noise ratio but also in a reduction in the motion artifacts.

In claim 2, if the complementary measured value has not been acquired in step c) then it is determined by means of John's equation. This produces CT images of particularly good quality.

John's equation is a known partial differential equation that, among other things, allows further measured values to be determined for measured values that have been acquired, which further measured values are consistent with those that have been acquired.

The term "consistent" can be explained as follows. The object in the examination region is not clearly defined by the set of measured values acquired in step c) because the measured values are affected by noise or also, for example, because too few measured values have been acquired. For the set of measured values, there are therefore a number of possible objects in the examination region that fit the measured values. A complementary measured value is consistent with the measured values that have been acquired when it can be produced by the passage of a ray through one of the possible objects. A consistency condition with which a complementary measured value of this kind can be determined is for example John's equation, which is known.

In claim 3, when the weighted complementary measured values and the respective weighted measured values belonging to them are added, a complementary measured value that has been obtained is given a heavier weighting if it was acquired in step c) rather than having been determined by, for example, John's equation. The greater account that is thereby taken of values that have actually been measured gives images of an improved quality.

Claims 4 and 5 describe a preferred exact computer tomography method that produces CT images of good quality for helical trajectories.

A computer tomograph for performing the method according to the invention is described in claim 6. Claim 7 defines a computer program for controlling the computer tomograph claimed in claim 6.

These and other aspects of the invention are apparent from and will be elucidated with reference to the embodiments described hereinafter.

Figure 1:
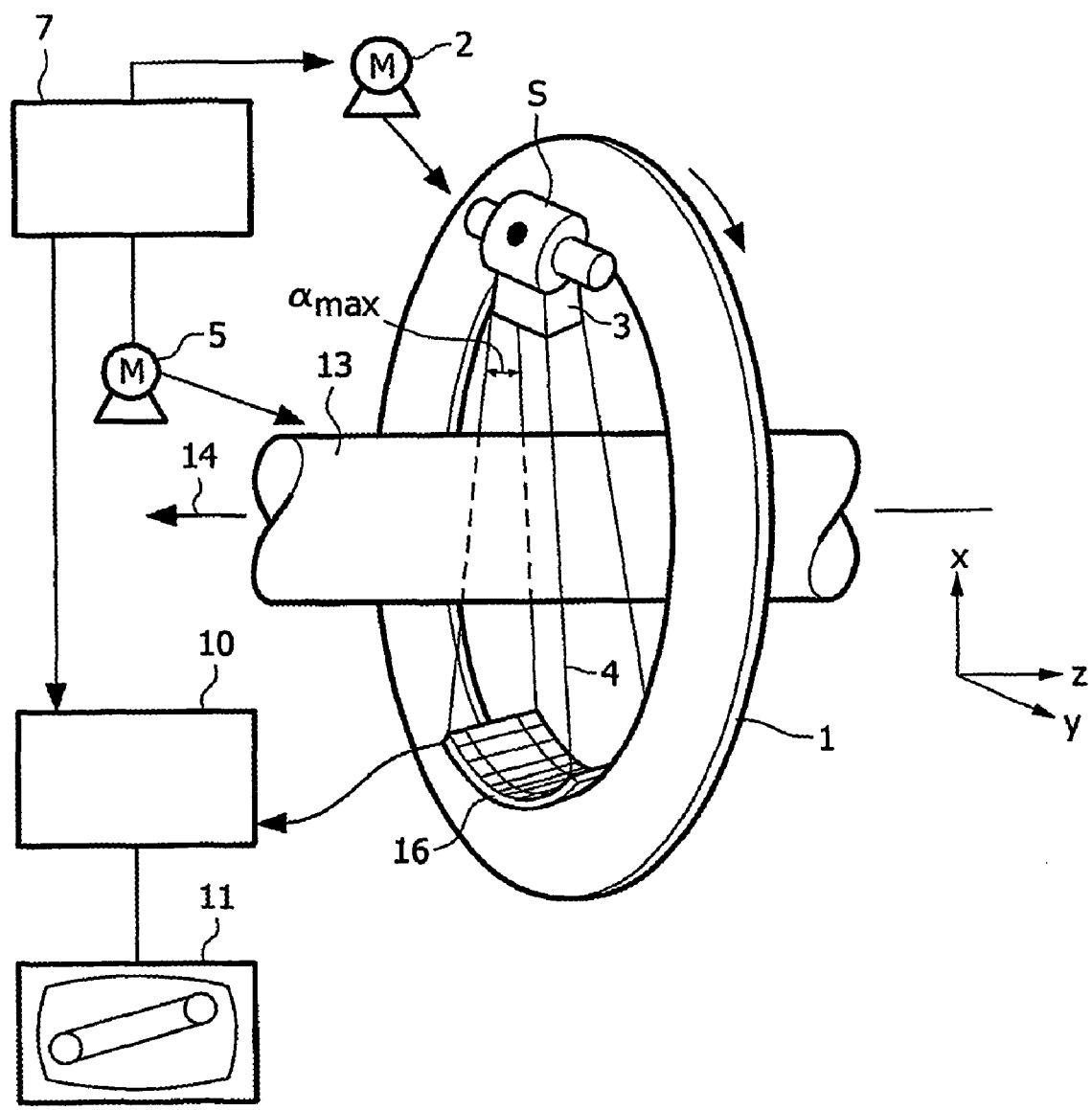
FIG. 1 is a schematic view of a special embodiment of computer tomograph with which a special embodiment of the method according to the invention can be performed.

The computer tomograph shown in FIG. 1 comprises a gantry 1 which is able to rotate about an axis of rotation 14 extending parallel to the z direction of the coordinate system shown in FIG. 1. For this purpose, the gantry 1 is driven by a motor 2 at an angular velocity that is preferably constant, but adjustable. Fastened to the gantry 1 is a radiation source S such as an X-ray generator, for example. This is provided with a collimator arrangement 3 that extracts from the radiation produced by the radiation source S a conical beam of rays 4, i.e. a beam of rays that is of a finite extent other than zero both in the z direction and also in a direction perpendicular thereto (i.e. in a plane perpendicular to the axis of rotation).

The beam of rays 4 passes through a cylindrical examination region 13 in which an object, e.g. a patient on a patient presentation table (neither of which is shown) or even a technical object, may be situated. Having passed through the examination region 13, the beam of rays 4 impinges on a detector unit 16 fastened to the gantry 1, which detector unit 16 has a face that comprises a plurality of detector elements that, in this embodiment, are arranged in the form of a matrix in rows and columns. The columns of detector elements extend parallel to the axis of rotation 14. The rows of detector elements are situated in planes perpendicular to the axis of rotation and, in this embodiment, are situated on an arc about the radiation source S (thus forming a focus-centered detector unit). In other embodiments however, they may be differently configured, e.g. to describe an arc about the axis of rotation 14 or in a straight line. In any position of the radiation source, each detector element on which the beam of rays 4 impinges gives a measured value for one ray from the beam of rays 4.

The included angle of the beam of rays 4, which is designated $\alpha_{max}$, determines the diameter of the object cylinder within which the object being examined is situated when the measured values are being acquired. The included angle is defined in this case as the angle that is made with a plane defined by the radiation source S and the axis of rotation 14 by a ray that, in a plane perpendicular to the axis of rotation 14, is situated at the edge of the beam of rays 4. The examination region 13, i.e. the object or the patient presentation table, can be displaced by means of a motor 5 parallel to the axis of rotation 14, i.e. to the z axis. However, to give an equivalent action, the gantry could equally well be displaced in this direction. When the object is a technical one rather than a patient, it can be rotated in the course of an examination while the radiation source S and the detector unit 16 remain stationary.

If the motors 2 and 5 run simultaneously, the radiation source S and the detector unit 16 describe a helical trajectory relative to the examination region 13. If on the other hand the motor 5 for advance in the direction of the axis of rotation 14 does not run and the motor 2 causes the gentry to rotate, a circular trajectory is produced for the radiation source S and the detector unit 16 relative to the examination region 13. In the present embodiment, only the helical trajectory will be considered. The method according to the invention could, however, also be applied where the trajectory was circular.

The measured values acquired by the detector unit 16 are fed to a reconstructing computer 10 that is connected to the detector unit 16 by, for example, a data transmission system (not shown) that operates without electrical contacts. The reconstructing computer 10 reconstructs the CT image and reproduces it, on a monitor 11, for example. The two motors 2 and 5, the reconstructing computer 10, the radiation source S and the transfer of the measured values from the detector unit 16 to the reconstructing computer 10 are controlled by a control unit 7.

Figure 2:
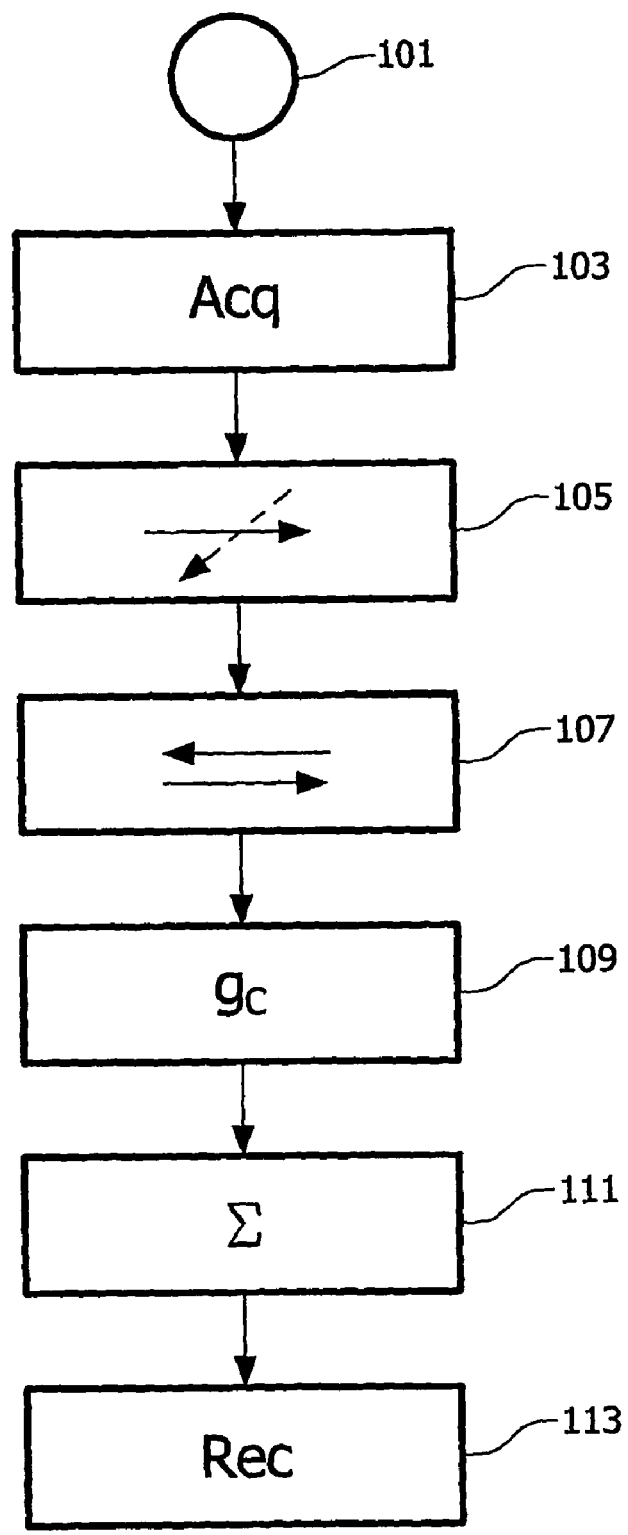
FIG. 2 is a flow chart of the method according to the invention.

FIG. 2 shows the flow of a method of measurement and reconstruction that can be performed with the computer tomograph shown in FIG. 1.

After initialization in step 101, the gantry rotates at an angular velocity that is constant in the present embodiment. The velocity may however equally well vary, e.g. as a function of time or of the position of the radiation source.

In step 103, the examination region, i.e. the object or the patient presentation table, is displaced parallel to the axis of rotation and the radiation from the radiation source S is switched on, thus enabling the detector unit 16 to detect the radiation in a plurality of angular positions. In the course of this, the radiation source S moves relative to the examination region along a helical trajectory of which the parameters can be defined by $$y(\lambda) = \begin{pmatrix} R\cos\lambda \\ R\sin\lambda \\ h\lambda \end{pmatrix} \quad (1)$$

Here, $2\pi h$ is the feed of the table per rotation, $\lambda$ is the angular position of the radiation source relative to a reference angular position that is any desired angular position but fixed, and R is the radius of the helical trajectory 17.

Figure 3:
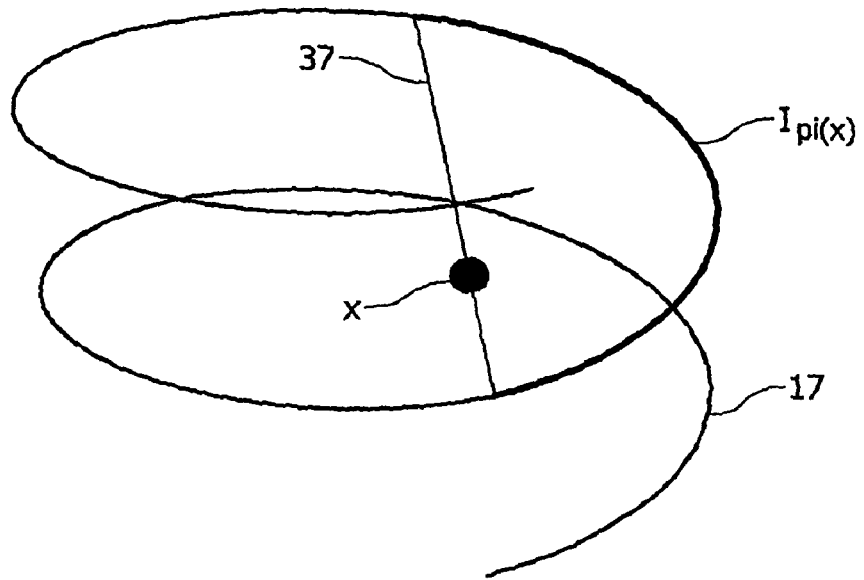
FIG. 3 shows a PI straight line and a PI interval for a point in the examination region.
Figure 4:
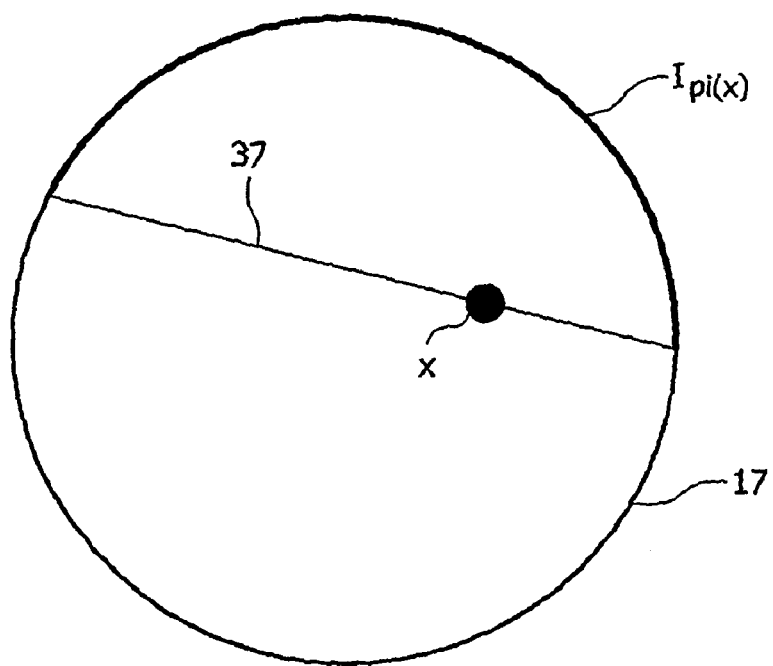
FIG. 4 shows a PI straight line and the PI interval for a point in the examination region, when projected onto a plane perpendicular to the axis of rotation.

In the present embodiment, the advance per rotation is selected to be such that, from any point x in the examination region, the radiation source S is visible over an angular range of at least 180°. The picking up of measured values with a table advance of this kind is referred to as PI acquisition PI acquisition will be explained in detail in what follows. For this purpose, there are shown in FIG. 3 the helical trajectory 17 along which the radiation source moves relative to the point x in the examination region, and the section $I_{PI}(x)$ of the helix 17 that is cut off by a PI straight line 37. FIG. 4 shows the helix 17 from FIG. 3 projected onto a plane oriented perpendicularly to the axis of rotation. The PI straight line 37 is that line which cuts the helix at two points and the point x, with the section $I_{PI}(x)$ of the helix that is cut off by the straight line extending through an angle of less than $2\pi$. In PI acquisition, rays that start from the radiation source S while the latter is on section $I_{PI}(x)$ of the helix pass through the point x.

In the context of the present embodiment, what is used below is a method of reconstruction that employs only measured values whose associated rays originate from section $I_{Pf}(x)$ of the helix, i.e. the measured values used are only ones that lie in what is called the PI interval. It is known that, by considering the geometry, it can be shown that measured values whose rays start from a given section of the helix lie within a reconstruction window on the detector unit. In the present PI acquisition, the reconstruction window is the PI window. The PI window 25 is bounded on a planar detector 60 by the PI lines 21, 23 that are defined by the following equations:

$$v(u) = +\frac{h}{2\pi}\left(1 + \left(\frac{u}{R}\right)^2\right)\left(\frac{\pi}{2} - \arctan\frac{u}{R}\right) \quad (1)$$

and $$v(u) = -\frac{h}{2\pi}\left(1 + \left(\frac{u}{R}\right)^2\right)\left(\frac{\pi}{2} + \arctan\frac{u}{R}\right) \quad (2)$$

Figure 5:
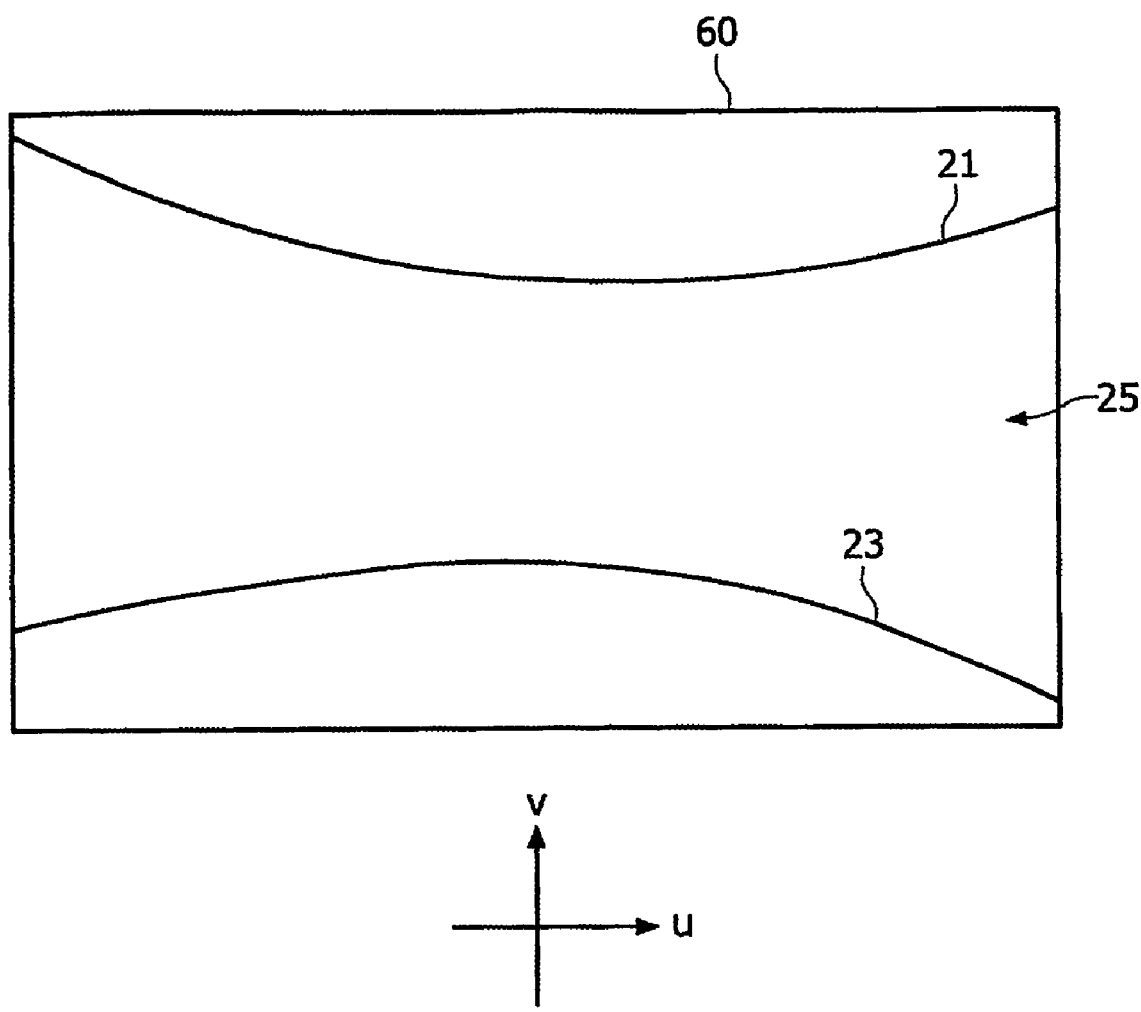
FIG. 5 is a schematic view of a planar detector having a PI window.

Here, u and v are coordinates on the planar detector 60 in the coordinate system shown in FIG. 5. For reasons of clarity, the coordinate system has been shown below the planar detector 60. However, the origin of the coordinate system is situated at the center of the detector. The unit vectors of the coordinate system are $1_u = (-\sin\lambda, \cos\lambda, 0)$ and $1_v = (0, 0, 1)$.

The planar detector 60 is an imaginary detector that contains the axis of rotation 14 and is oriented perpendicularly to that ray that, starting from the position of the radiation source at the time, strikes the axis of rotation 14 perpendicularly. Measured values that are detected by the actual detector unit 16 can be projected onto the planar detector 60 along their corresponding rays.

Computer tomography methods of the kind defined in the opening paragraph use only measured values that lie within a reconstruction window. The rest of the measured values are not used and this leads to a poor signal-to-noise ratio and motion artifacts. In the following steps, a complementary measured value $g_c(\lambda_0, u_0, v_0)$ is determined, for each measured value $g(\lambda_0, u_0, v_0)$ that lies within the reconstruction window, with the help of redundant data, i.e. measured values that lie outside the reconstruction window, as a result of which the signal-to-noise ratio is improved and the motion artifacts reduced. The ray associated with the measured value $g(\lambda_0, u_0, v_0)$ is referred to below as the direct ray.

In other embodiments, a complementary measured value may be determined for each of only a proportion of the acquired measured values that lie within the reconstruction window. In particular, it would be possible for a complementary measured value to be determined only for those measured values that are situated in the edge regions of the reconstruction window.

A complementary measured value is defined by the path followed by the complementary ray belonging to it. A complementary ray follows a path parallel to the direct ray belonging to it but in the opposite direction thereto. A consistency condition can be used to determine the complementary measured value associated with the complementary ray. The consistency condition that is used in the present embodiment to determine the complementary measured value associated with the complementary ray is the equation generally referred to as John's equation that was published in "Partial Differential Equations", F. John, Applied Mathematical Sciences, Springer-Verlag, 1971 and that has been adapted for helical trajectories in U.S. Pat. No. 6,292,526 B1.

In accordance with the invention, the method used to determine a complementary measured value may be any method, and in particular any consistency condition, that, by taking account of redundant measured values, allows a complementary measured value to be determined, at least approximately, for a complementary ray that follows a path parallel to the direct ray but in the opposite direction thereto.

Figure 6:
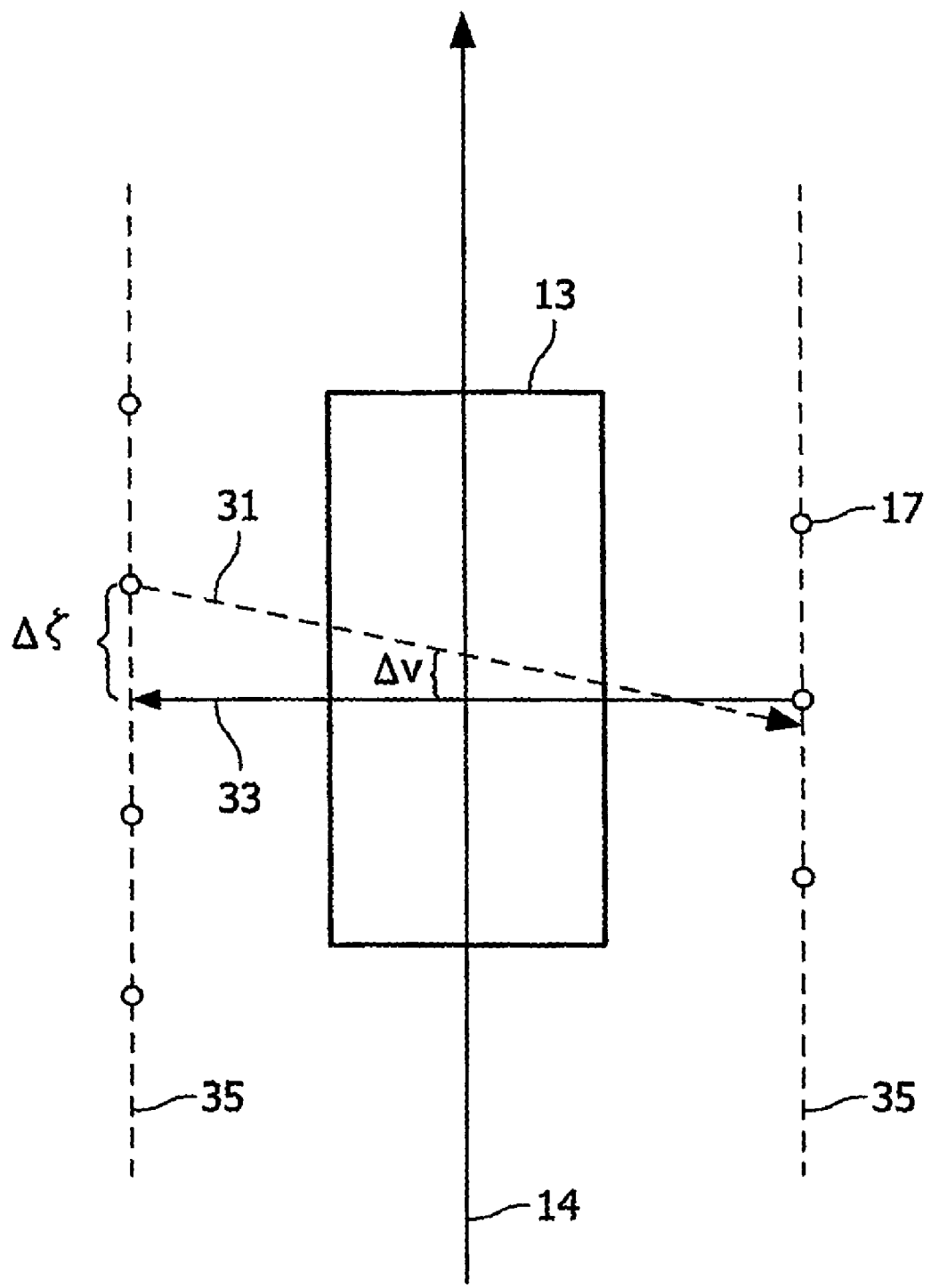
FIG. 6 is a schematic view in cross-section of a helical trajectory and of an examination region, showing a direct ray and a complementary ray.

To determine the particular complementary measured value $g_c(\lambda_0, u_0, v_0)$, in step 105 an approximating measured value $g(\lambda_1, u_1, \tilde{v}_1)$, whose associated approximating ray 31 follows approximately the same path as the complementary ray (see FIG. 6), is first determined from the acquired measured values. This approximating ray starts from the angular position $\lambda 1$ and impinges on the planar detector 60 at a point $(u_1, \tilde{v}_1)$.

The angular position of the approximating ray is defined by $$\lambda_1 = \begin{cases} \lambda_0 + \pi - 2\beta & \text{where } v_0 > 0 \\ \lambda_0 - \pi - 2\beta & \text{where } v_0 < 0 \end{cases} \quad (3)$$

Here, β is the fan angle of the direct ray, i.e. the angle that the direct ray makes with a ray that intersects the planar detector 60 in FIG. 5 in the center. The angular position $\lambda_1$ is the angular position at which a direct ray that starts from the position $y(\lambda_0)$ of the radiation source and impinges on the planar detector at a point $(u_0, v_0)$, first touches the helix 17 if the ray is displaced parallel to the axis of rotation 14.

The equation that governs the u coordinate of the approximating ray on the planar detector 60 is:

$$u_1 = -u_0 \quad (4)$$

The v coordinate is determined as follows. By $\lambda = \lambda_1$ and $u = u_1$ is defined a fan of rays that starts from the angular position $\lambda_1$ on the helix 17 and impinges on all those detector elements for which $u = u_1$ is true. The respective point of intersection with the direct ray 33 is determined for each ray in this fan of rays. The approximating ray 31 is then that ray in the fan of rays whose point of intersection is closest to the axis of rotation 14. This approximating ray impinges on the planar detector at a point $(u_1, \tilde{v}_1)$, where $$\tilde{v}_1 = \begin{cases} \frac{\sqrt{u_1^2 + R^2}}{R}\left[h(2\beta - \pi)\left(\frac{1}{2\cos\beta} - \frac{\sqrt{u_1^2 + R^2}}{R}\right) - 2v_0\cos\beta\right] & \text{where } v_0 > 0 \\ \frac{\sqrt{u_1^2 + R^2}}{R}\left[h(2\beta + \pi)\left(\frac{1}{2\cos\beta} - \frac{\sqrt{u_1^2 + R^2}}{R}\right) - 2v_0\cos\beta\right] & \text{where } v_0 < 0 \end{cases} \quad (5)$$

In step 107, the path followed by the complementary ray is determined. As has already been explained above, the complementary ray follows a path parallel, but in the opposite direction, to the direct ray 33. The direct ray 33 impinges on the surface 35 of the cylinder that is defined by the helical trajectory 17 at a point $$z = z_0 = h\lambda_0 + v_0 \frac{2R\cos\beta}{\sqrt{u_1^2 + R^2}}. \quad (6)$$

During the acquisition of the approximating measured value, the radiation source S was situated at a point $$z = z_1 = h\lambda_1 = \begin{cases} h(\lambda_0 + \pi - 2\beta) \text{ where } v_0 > 0 \\ h(\lambda_0 - \pi - 2\beta) \text{ where } v_0 < 0 \end{cases} \quad (7)$$

To allow a complementary ray to be obtained, the position $z_1$ of the radiation source has to be "shifted" to the position $z_0$. It must therefore be shifted by $$\Delta\varsigma = z_1 - z_0 = \begin{cases} h(+\pi - 2\beta) - v_0 \dfrac{2R\cos\beta}{\sqrt{u_1^2 + R^2}} \text{ where } v_0 > 0 \\ h(-\pi - 2\beta) - v_0 \dfrac{2R\cos\beta}{\sqrt{u_1^2 + R^2}} \text{ where } v_0 < 0 \end{cases} \quad (8)$$

The position of the radiation source for the complementary ray is thus that position of the radiation source which is defined by the angular position $\lambda_1$ and has been shifted along the axis of rotation by $\Delta\varsigma$.

The complementary ray that starts from that radiation source position of the approximating ray which has been shifted by $\Delta\varsigma$ must impinge on the surface of the cylinder at the z position from which the associated direct ray starts. This produces the following defining equation for the coordinate $v_1$ of the complementary ray:

$$h\lambda_0 = h\lambda_1 + v_1 \frac{2R\cos\beta}{\sqrt{u_1^2 + R^2}} \quad (9)$$

By inserting equating (3), this gives $$v_1 = \begin{cases} h(2\beta - \pi)\dfrac{\sqrt{u_1^2 + R^2}}{2R\cos\beta} \text{ where } v_0 > 0 \\ h(2\beta + \pi)\dfrac{\sqrt{u_1^2 + R^2}}{2R\cos\beta} \text{ where } v_0 < 0 \end{cases} \quad (10)$$

The complementary ray is therefore found from the approximating ray by shifting the radiation source along the axis of rotation by $\Delta\varsigma$ and by shifting the point of impingement of the ray on the detector by $$\Delta v = v_1 - \tilde{v}_1 = -\Delta\varsigma \frac{R^2 + u_1^2}{R^2}. \quad (11)$$

The u coordinate of the complementary ray is equal to the corresponding coordinate of the approximating ray.

Once the path followed by the complementary ray complementary to a direct ray is known, the complementary measured value associated with the complementary ray can be determined in step 109. If the complementary measured value was acquired, the measured value acquired can be used as a complementary measured value. This is not generally the case however, because the radiation source position of the complementary ray is usually not situated on the helix 17.

From "Improved 2D rebinning of helical cone-beam CT data using John's equation", Defrise, Noo, Kudo, M10-74 in 2002 Nuclear Science Symposium Conference Record, guest editor Scott Metzler, 10-16 November, Norfolk, Va., USA, ISBN 0-7803-7637-4, it is known that, with the help of John's equation, a complementary measured value that is consistent to a good approximation with the measured values can be calculated by adding a correcting measured value to the approximating measured value. The correcting measured value $\Delta g(\lambda_1, u_1, \tilde{v}_1)$ is given by the following equation:

$$\Delta g(\lambda_1, u_1, \tilde{v}_1) = \frac{\Delta\varsigma}{R} \quad (12)$$
$$\int_{-\infty}^{u_1} du' \left( \frac{\partial g(\lambda, u, v)}{\partial \lambda \partial v} + \frac{Ru'v - h(R^2 + u'^2)}{R^2} \frac{\partial g(\lambda, u, v)}{\partial^2 v} \right) \bigg|_{\lambda = \lambda_1, v = \tilde{v}_1}.$$

In accordance with the invention, all or only a proportion of the measured values acquired can be used to determine the correcting measured value from equation (12). In the present embodiment, the measured values used are only ones whose associated rays start from radiation source positions $y(\lambda)$ that are located on the helix 17 in the vicinity of the radiation source position $y(\lambda_1)$ of the approximating ray. What that means is that the measured values used are only ones whose associated radiation source positions are situated in the range $y(\lambda)$ where $\lambda_1 - \Delta_\lambda < \lambda < \lambda_1 + \Delta_\lambda$. In the present case, $\Delta_\lambda$ is selected to be such that ten different radiation source positions $y(\lambda)$ are covered. In other embodiments a different number of radiation source positions, and hence of measured values, can be used.

The range $\Delta_\lambda$ is selected to be at least sufficiently wide for redundant measured values to contribute to at least some complementary measured values. However, in the majority of cases this condition will already have been met due to the fact that the approximating measured value is itself redundant.

To determine the correcting measured value, all the measured values whose associated rays start from radiation source positions that are within the above range are derived from equation (12) by their angular positions λ and their v coordinate, to allow a first dataset of partial derivatives to be derived from equation (12). These derivations, and the following ones too, may be performed by, for example, the finite difference method. Also, the original measured values, i.e. the non-derived ones, whose associated rays start from radiation source positions that are within the above range are twice derived as partial derivatives, for v, to allow a second dataset of derivatives to be obtained.

The measured values in the second dataset of derivatives are then multiplied by a weighting factor that follows a square law in u and is linear in v. In the present embodiment, this weighting factor is equal to $$\frac{Ruv - h(R^2 + u^2)}{R^2}. \quad (13)$$

The next step is to add the measured values in the first and second datasets of derivatives to give a set of measured values, and those resulting values whose associated rays start from the angular position $\lambda_1$ and impinge on row $\tilde{v}_1$ of the detector unit and on columns whose coordinates u are equal to or smaller than $u_1$, are added up.

Finally, the resulting sum is multiplied by a factor that is proportional to $\Delta\zeta$ and inversely proportional to R. The sum is preferably multiplied by $\Delta\zeta/R$. The sum multiplied by the correcting factor is the correcting measured value for the approximating measured value $g(\lambda_1,u_1,\tilde{v}_1)$, or for the measured value $g(\lambda_0,u_0,v_0)$ of the direct ray.

The correcting measured value having been calculated, the complementary measured value $g_c(\lambda_0,u_0,v_0)$ to the measured value $g(\lambda_0,u_0,v_0)$ can be determined from $$g_c(\lambda_0,u_0,v_0)=g(\lambda_1,u_1,\tilde{v}_1)+\Delta g(\lambda_1,u_1,\tilde{v}_1)$$

by adding the correcting measured value to the approximating measured value.

Once steps 105 to 109 have been performed for all the measured values $g(\lambda_0,u_0,v_0)$ that lie within the PI window, two sets of measured values exist, i.e. the dataset acquired in step 103 and the dataset complementary thereto.

In step 111, each measured value for which a complementary measured value has been determined is replaced by a sum comprising the complementary measured value after it has been weighted and the associated measured value after it has been weighted. For this purpose, the given measured value is added to the associated complementary measured value, each value having been multiplied by a weighting factor prior to the addition. If the complementary measured value was acquired, then it and the associated measured value are weighted by equal amounts, and in particular are each multiplied by 0.5. If the complementary measured value was determined from a consistency condition, such as John's equation for example, then it is multiplied by a smaller weighting factor than the associated measured value. In this way, the measured value may be multiplied by 0.9 or 0.8 for example, whereas the complementary measured value is multiplied by 0.1 or 0.2. In the present embodiment, the sum of a measured value/complementary measured value pairing is equal to 1.

Figure 7:
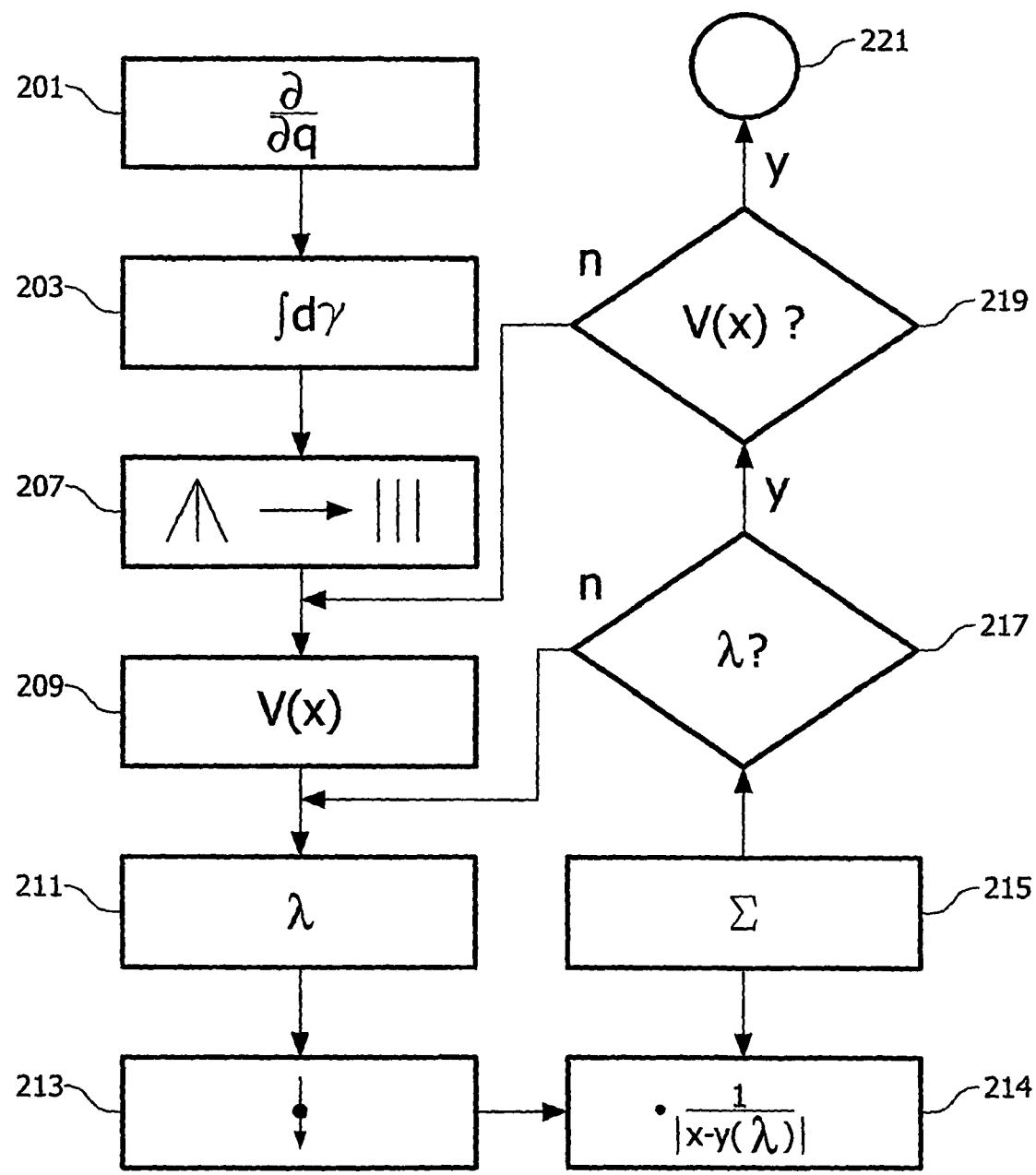
FIG. 7 is a flow chart for an exact reconstruction of a CT image.

In the next step 113, a CT image, which in this embodiment is an image of the distribution of absorption in the examination region, is reconstructed by an exact method from the measured values lying within the PI window that were determined in the previous steps, i.e. in particular from the measured values that have been obtained by adding weighted complementary measured values and associated measured values. The individual steps in the reconstruction are shown in FIG. 7.

In other embodiments, a complementary measured value could also have been determined for only a proportion of the measured values that lie within a reconstruction window. If this were the case, then what would be used for the reconstruction would be, on the one hand, the measured values lying within the reconstruction window that had been obtained by adding a weighted complementary measured value and a weighted measured value or, on the other hand, if no complementary measured values had been determined for some of the measured values lying within the reconstruction window, the measured value that was acquired in the particular case.

To allow the exact reconstruction to be understood, the following equation from E1 will first be cited:

$$f(x) = -\frac{1}{2\pi^2}\int_{I_{Pt}(x)} ds \frac{1}{|x-y(\lambda)|}\int_{-\pi}^{\pi} \frac{d\gamma}{\sin\gamma}\frac{\partial}{\partial q}D_f(y(q),\Theta(s,x,\gamma))|_{q=\lambda}. \quad (15)$$

This equation describes an exact reconstruction of absorption by back-projection of the measured values. In it, $f(x)$ is the spatial distribution of absorption in the examination region at point x.

The measured value $Df(y,\Theta)$ can be defined by the line integral:

$$D_f(y(\lambda),\Theta) = \int_0^\infty dl f(y+l\Theta) \quad (16)$$

Here, the unit vector $\Theta$ gives the direction of the ray belonging to the measured value.

Figure 8:
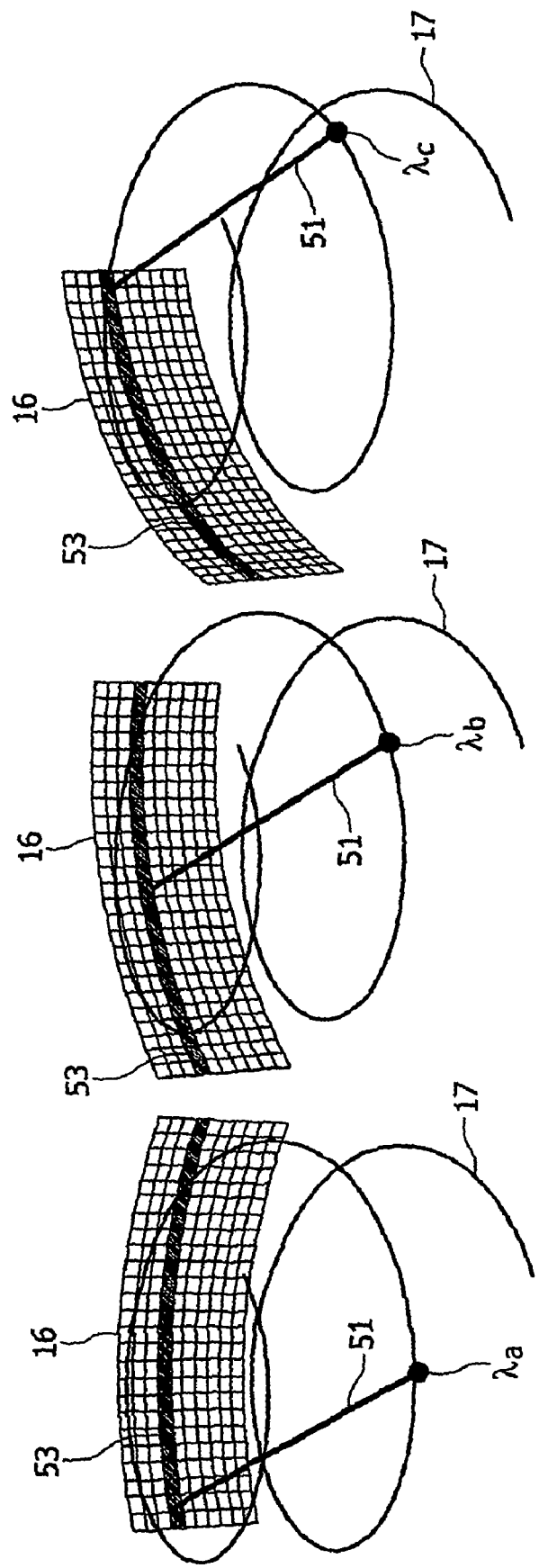
FIG. 8 is a schematic perspective view of parallel rays in different positions.

In step 201, the measured values are derived as partial derivatives from equation (15) for q, i.e. for the angular position of the radiation source at the point $q=\lambda$. It should be borne in mind in this case that only y depends on q and not $\Theta$, which means that, for the derivation, account has to be taken of measured values from parallel rays in each case. Because parallel rays have the same cone angle, then, as shown in FIG. 8, in the case of the focus-centered detector 16 that is used in the present case, the parallel rays 51 impinge on the same row 53 in the detector. In this case the cone angle of a ray is the angle that the ray makes with a plane perpendicular to the axis of rotation 14. For the partial derivation, the measured values may first be resorted. For this purpose, measured values that belong to parallel rays, i.e. to the same row 53 in the detector but to different angular positions $\lambda_a, \lambda_b, \lambda_c$ of the radiation source, are combined in each case to form a set. The measured values in each set are derived, numerically for example by the finite difference method, in accordance with the angular position of the radiation source.

Figure 9:
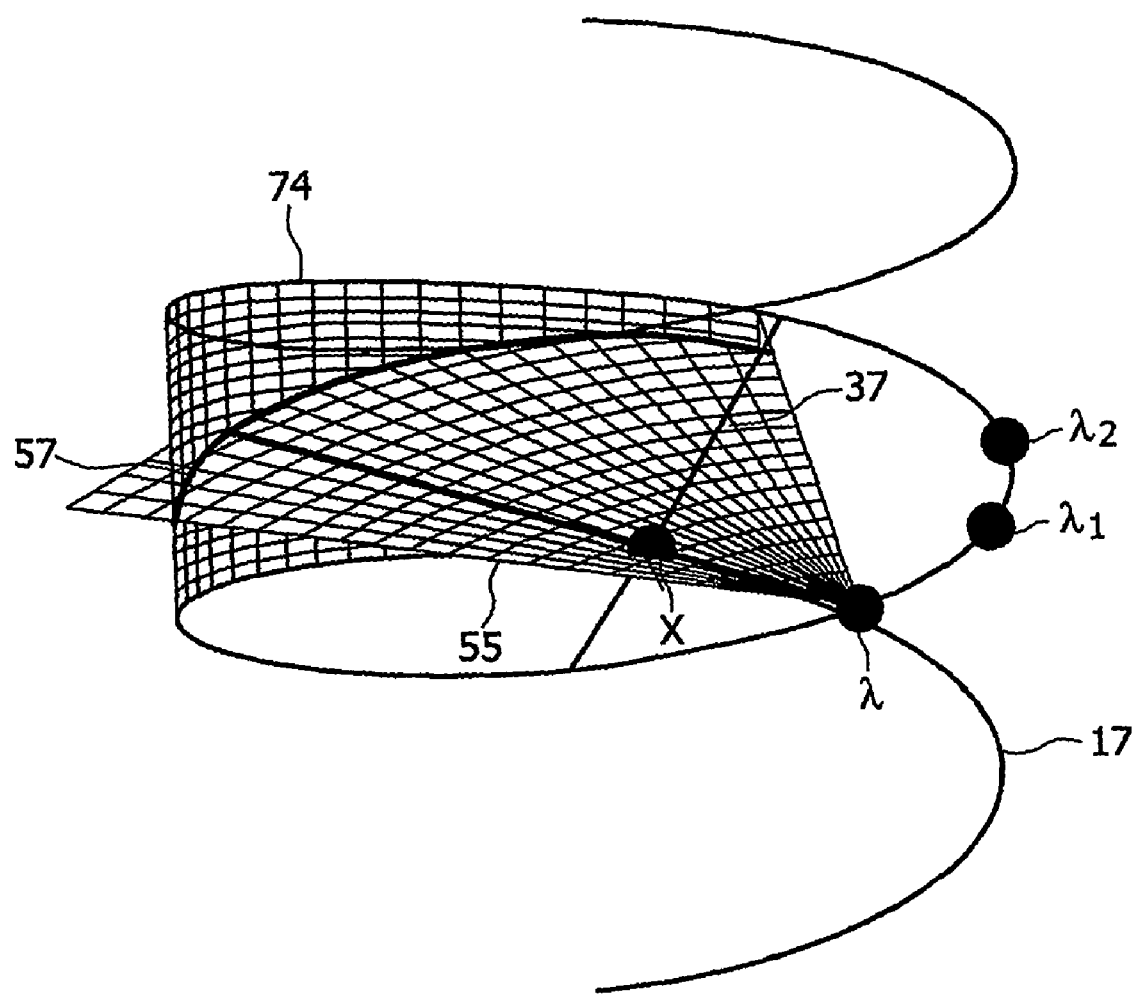
FIG. 9 is a schematic perspective view of the helical trajectory showing a κ plane and a κ line.

The unit vector $\Theta$ depends on the $\kappa$ angle $\gamma$ that can be defined by means of so-called $\kappa$ planes 55 (see FIG. 9). The $\kappa$ planes 55 will be explained below.

To allow a $\kappa$ plane 55 to be determined, a function $$\lambda_1(\lambda,\lambda_2) = \begin{cases} \dfrac{m\lambda_2 + (n-m)\lambda}{n}, & \lambda \le \lambda_2 < \lambda + 2\pi \\[6pt] \dfrac{m\lambda + (n-m)\lambda_2}{n}, & \lambda > \lambda_2 > \lambda - 2\pi \end{cases} \quad (17)$$

is introduced that depends on non-negative values n and m, n>m, that are whole numbers. In the present embodiment, n is selected to be equal to 2 and m to 1. Other values could however also be selected for n, m. Equation (15) would still remain exact; only the positions of the κ planes 55 would change. Also defined are the vector function $$u(\lambda, \lambda_2) = \begin{cases} [y(\lambda_1(\lambda, \lambda_2)) - y(\lambda)] \times \\ \dfrac{[y(\lambda_2) - y(\lambda)]}{[y(\lambda_1(\lambda, \lambda_2)) - y(\lambda)] \times} \cdot sgn(\lambda_2 - \lambda), \ 0 < |s_2 - s| \\ [y(\lambda_2) - y(\lambda)] \\ \dfrac{\dot{y}(\lambda) \times \ddot{y}(\lambda)}{|\dot{y}(\lambda) \times \ddot{y}(\lambda)|}, \ \lambda_2 = \lambda \end{cases} \quad (18)$$

and the unit vector $$\beta(\lambda, x) = \frac{x - y(\lambda)}{|x - y(\lambda)|}. \quad (19)$$

The vector β points from the radiation source position y(λ) to position x. To determine the κ plane, a value $\lambda_2 \in I_{Pl}(x)$ is selected such that yλ, $y(\lambda_1,\lambda,\lambda_2)$, $y(\lambda_2)$ and x lie in a plane. This plane is referred to as the κ plane 55 and the line of intersection between the κ plane 55 and the face 74 of the detector is referred to as the κ line 57. In FIG. 9, the detector 74 is bounded by two successive turns of the helical trajectory 17 and is of the same curvature as the helix 17. This detector has been used here as an example to make things clearer. Corresponding lines of intersection 57 can be determined for other detectors, such as the focus-centered or the planar detector. In FIG. 9 is shown a fan-shaped part of a κ plane. The edges of the fan meet at the location of the radiation source. Defining the κ plane 55 in this way is equivalent to solving the equation $$(x - y(\lambda)) \cdot u(\lambda, \lambda_2) = 0, \ \lambda_2 \in I_{Pl(x)} \quad (20)$$

for $\lambda_2$·u is thus the normal vector of the κ plane 55. To allow the vector function Θ(λ,x,γ) to be determined, the vector $$e(\lambda, x) = \beta(\lambda, x) \times u(\lambda, x) \quad (21)$$

is defined. With the definitions for β and e, the vector function Θ(λ,x,γ) can then be stated as follows:

$$\Theta(\lambda, x, \gamma) = \cos \gamma \cdot \beta(\lambda, x) + \sin \gamma \cdot e(\lambda, x) \quad (22)$$

Because the two vectors β and e are oriented perpendicularly to u, the κ angle γ gives the direction of the vector Θ and hence the direction of a ray within a κ plane.

κ planes and κ lines are described in detail in E1, which is hereby incorporated by reference.

In step 203, the derived measured values along κ lines are multiplied in equation (15) by a weighting factor that decreases as the sine of the κ angle increases and in particular is equal to the reciprocal of the sine of the κ angle, and are added up. For this purpose, a κ line is determined for each point x in the examination region and for each radiation source position λ, in which case, as explained above, a value $\lambda_2 \in I_{Pl}(x)$ is selected such that yλ, $y(\lambda_1,\lambda,\lambda_2)$, $y(\lambda_2)$ and x lie in a plane, the κ plane. The κ line is then determined as the line of intersection between the κ plane and the face of the detector. The multiplications by the weighting factor and the integrations or additions may be performed by means of, for example, a Fourier transformation.

The derived and integrated measured values can be represented by the following equation:

$$p(y(\lambda \Phi(\lambda, x)) = \int_{-\pi}^{\pi} \frac{d\gamma}{\sin\gamma \partial q} \frac{\partial}{\partial q} D_f(y(q), \Theta(\lambda, x, \gamma))|_{q=\lambda}. \quad (23)$$

In this equation, p(y(λ), Φ(λ,x)) are the derived and integrated measured values and Φ(λ,x) is a unit vector that points from the radiation source position y(λ) towards point x in the examination region.

The integration step that is missing in equation (15), i.e. the back-projection of the measured values, can then be defined by the following equation:

$$f(x) = -\frac{1}{2\pi^2} \int_{I_{Pl}(x)} d\lambda \frac{1}{|x - y(\lambda)|} p(y(\lambda), \Phi(\lambda, x)). \quad (24)$$

Before the back-projection, a rebinning of the measured values can take place in step 207. The rebinning causes the measured values to be resorted and reinterpolated as if they had been measured with a different radiation source (an extended radiation source, located on a part of a helix, that is able to emit fans of rays each parallel to one another).

This will be explained in detail by reference to FIG. 10. In this Figure, 17 denotes the helical trajectory from which the radiation source passes its rays through the examination region. Reference numeral 43 denotes a fan-shaped beam of rays that starts from the radiation source position $S_0$ and whose rays extend along paths in a plane containing the axis of rotation 14. The conical beam of rays that is emitted by the radiation source at the position $S_0$ can be thought of as composed of a plurality of plane fans of rays that are situated in planes parallel to the axis of rotation 14 and that intersect at the radiation source position $S_0$. Of these fans of rays FIG. 10 shows only one, namely fan of rays 43.

Figure 10:
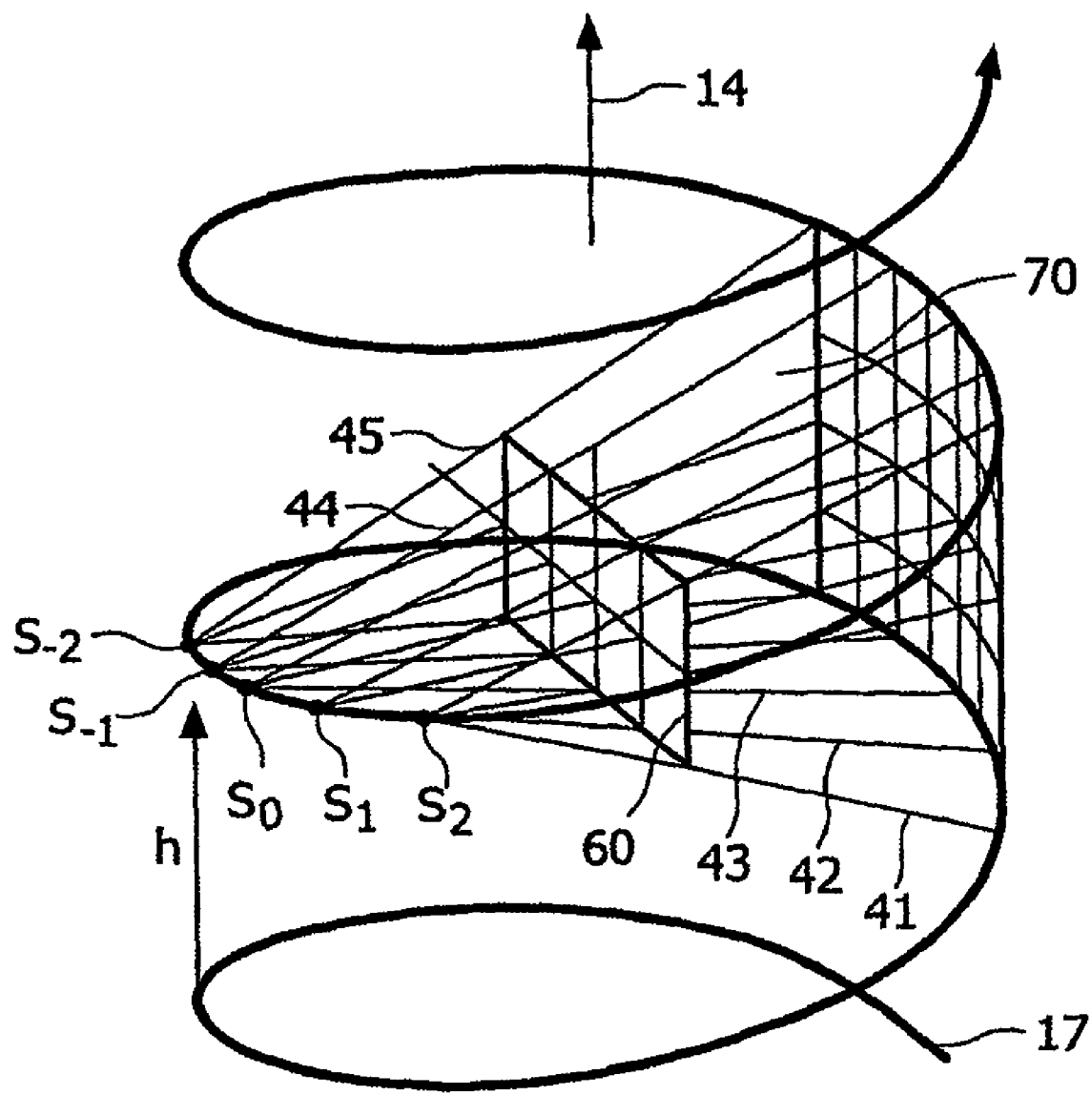
FIG. 10 is a schematic perspective view of the helical trajectory showing, in parallel planes, fans of rays formed by rebinning.

Also shown in FIG. 10 are further fans of rays 41, 42 and 44, 45 that are parallel to fan of rays 43 and that lie in planes parallel to one another and to the axis of rotation 14. The associated radiation source positions $S_{-2}$, $S_{-1}$ and $S_1$, $S_2$ are occupied by the radiation source S respectively before and after it has reached radiation source position $S_0$. All the rays in the fans of rays 41 to 45 have the same angle of projection. The fans of rays 41 to 45 define a beam of rays of a tent-like shape.

The measured values obtained after the rebinning are then used to reconstruct the distribution of absorption in the examination region by means of a back-projection, carried out with equation (23) in the present embodiment.

For this purpose, in step 209 a voxel V(x) within a presettable region (the field of view (FOV)) in the examination region, and a PI interval $I_{Pl}(x)$ for this voxel, are determined. Then, in step 211, an angular position λ within the interval $I_{Pl}(x)$ is preset. In step 213, a check is made to see whether a measured value whose ray passes through the center of the voxel V(x) is available for the angular position λ. If no such ray can be found, then it is found at what point a central ray would have impinged on the face of the detector. The associated measured value is then calculated by interpolation from the measured values from adjacent rays. The measured value that can be assigned to the ray passing though the voxel, or the measured value obtained by interpolation, as the case may be, is multiplied in step 214 by a weighting factor that becomes smaller as the distance between the radiation source y(λ) and the point x to be reconstructed in the examination region increases. In the present embodiment, this weighting factor is, as shown in equation (24), equal to $1/|x-y(\lambda)|$. In step 215, the weighted measured value is summed to give the voxel V(x). In step 217 a check is made to see whether all the angular positions λ in the interval $I_{PI}(x)$ have been looked at. If they have not, the flow chart branches back to step 211. Otherwise, a check is made in step 219 to see whether all the voxels V(x) in the FOV have been covered. If they have not, the sequence continues with step 209. If on the other hand all the voxels V(x) in the FOV have been covered, then the absorption in the whole of the FOV, and hence the CT image, has been determined, and the exact reconstruction of the CT image comes to an end in step 221.

As has already been mentioned above, in other embodiments the radiation source may also move along a circular trajectory relative to the examination region. If, in a case of this nature, the measured values used to reconstruct a CT image are only ones that lie within a reconstruction window, then in this case too complementary measured values can be determined for at least some measured values, in particular by means of John's equation. As was described above for the helical trajectory, a sum replaces the measured value in the acquired dataset is formed from a measured value/complementary measured value pairing. Finally, a CT image can be reconstructed by known methods of reconstruction from the data that has been obtained in this way.

A computer tomography method in which the radiation source moves relative to the examination region along a circular trajectory and the measured values used are solely ones that lie within a reconstruction window is known from, for example, "A fast and efficient method for sequential cone-beam CT", Koehler, Proksa, Grass, Medical Physics, vol. 28, no. 11, pp. 2318-2327.

LIST OF REFERENCE NUMERALS $\alpha_{max}$ Included angle
$\lambda, \lambda_1, \lambda_2, \lambda_a, \lambda_b, \lambda_c$ Angular positions of the radiation source on the helical trajectory
$\Delta\zeta$ Shift in the z direction
$\Delta v$ Shift in the v direction
x Point in the examination region
$I_{PI}(x)$ Section of helix
S Radiation source
$S_{-2}, S_{-1}, S_0, S_1, S_2$ Positions of radiation source
1 Gantry
2, 5 Motors
3 Collimator arrangement
4 Beam of rays
7 Control unit
10 Image processing computer
11 Monitor
13 Examination region
14 Axis of rotation
16 Detector unit
17 Helical trajectory
21, 23 PI lines
25 PI window
31 Approximating ray
33 Direct ray
35 Surface of cylinder
37 PI straight line
41, 42, 43, 44, 45 Mutually parallel fans of rays
51 Parallel rays
53 Row on detector
55 κ plane
57 κ line
60 Planar detector
70 Beam of rays
74 Face of detector

The invention claimed is:

1. A computer tomography method having the following steps:
   a) generation, by a radiation source, of a conical beam of rays that passes through an examination region and an object situated therein,
   b) production of a relative movement between the radiation source on the one hand and the examination region on the other hand, which movement comprises at least a rotary movement about an axis of rotation and is in particular in the form of a helix or circle,
   c) acquisition, by a detector unit and during the relative movement, of measured values that depend on the intensity in the beam of rays on the farther side of the examination region,
   d) determination, with the help of redundant measured values, of a complementary measured value for each of at least some of the measured values that were acquired in step c) and that lie within a reconstruction window, the rays associated with the given measured value and the complementary measured value belonging to it being oriented in opposite directions to one another,
   e) replacement of each measured value for which a complementary measured value was determined in step d) by a sum comprising the measured value, having been weighted, and the complementary measured value, having been weighted,
   f) reconstruction of a CT image of the examination region from the measured values lying within the reconstruction window.

2. A computer tomography method as claimed in claim 1, wherein, if a ray that is associated with a complementary measured value from step d) follows the same path as a ray that is associated with a measured value that was acquired in step c), the complementary measured value is set to be equal to this measured value, and in that, if a ray that is associated with a complementary measured value from step d) does not follow the same path as one of the rays that are associated with the measured values that were acquired in step c), the complementary measured value in question is determined with the help of John's equation.

3. A computer tomography method as claimed in claim 1, wherein, prior to the addition in step e), the complementary measured value and the associated measured value are each multiplied by a weighting factor, the weighting factors for complementary measured value and the measured value belonging thereto being equal if the ray that is associated with the complementary measured value from step d) follows the same path as one of the rays that are associated with the measured values that were acquired in step c), and the weighting factor for a measured value being greater than the weighting factor for an associated complementary measured value if the ray that is associated with the complementary measured value from step d) does not follow the same path as one of the rays that are associated with the measured values that were acquired in step c).

4. A computer tomography method as claimed in claim 1, wherein, in step c) the relative movement is in the form of a helix and in that the reconstruction of a CT image in step f) comprises the following steps:
   partial derivation of measured values with which parallel rays having different radiation source positions are associated, for an angular position of the radiation source on the helix that is associated with the given measured with value, filtering of the derived measured values along κ lines, reconstruction of the CT image by back-projection of those filtered measured values that lie within a PI window.

5. A computer tomography method is claimed in claim 4, wherein the filtering of a measured value comprises the following steps:

determination of a κ line for the measured value, multiplication of those measured value that are situated on the κ line by a weighting factor that increases with the reciprocal of the sine of the κ angle-and in particular is equal to this reciprocal, adding up of the weighted measured values lying on the κ line, the resulting sum being the filtered measured value.

6. A computer tomograph having a radiation source for generating a conical beam of rays that passes through an examination region and an object situated therein, a drive arrangement to enable an object contained in the examination region and the radiation source to be caused to rotate relative to one another about an axis of rotation and to be displaced parallel to the axis of rotation, a detector unit coupled to the radiation source, that has a detector surface, for acquired measured values, a reconstructing unit for reconstructing a CT image within the examination region from the measured values acquired by the detector unit a control unit for controlling the radiation source, the detector unit the drive arrangement and the reconstructing unit in the following steps:

a) generation by the radiation source of a conical beam of rays that passes through the examination region and the object situated therein, b) production of a relative movement between the radiation source on the one hand and the examination region on the other hand, which movement comprises at least a rotary movement about the, axis of rotation and is in particular in the form of a helix or circle, c) acquisition, by the detector unit and during the relative movement, of measured values that depend on the intensity in the beam of rays on the farther side of the examination region, d) determination, with the help of redundant measured values, of a complementary measured value for each of at least some of the measured values that were acquired in step c) and that lie within a reconstruction window, the rays associated with the given measured value and the complementary measured value belonging to it being oriented in opposite directions, to one another, e) replacement of each measured value for which a complementary measured value was, determined in step d) by a sum comprising the measured value, having been weighted, and the complementary measured value, having been weighted, f) reconstruction of a CT image of the examination region from the measured values lying within the reconstruction window.

7. A computer readable medium encoded with a computer program for a control unit for controlling a radiation source, a detector unit, a drive arrangement and a reconstructing unit of a computer tomograph to perform in the following sequence:

a) generation,by the radiation source (S), of a conical beam of rays that passes through the examination region and the object situated therein, b) production of a relative movement between the radiation source on the one hand and the examination region on the other hand, which movement comprises at least a rotary movement about the axis of rotation and is in particular in the form of a helix or circle, c) acquisition, by the detector unit and during the relative movement, of measured values that depend on the intensity in the beam of rays on the farther side of the examination region, d) determination with help of redundant measured values, of a complementary measured value for each of at least some of the measured values that were acquired in step c) and that lie within a reconstruction window, the rays associated with the given measured value and the complementary measured value belonging to it being oriented in opposite directions to one another, e) replacement of each measured value for which a complementary measured value was determined in step d) by a sum comprising the measured value, having been weighted, and the complementary measured value, having been weighted, f) reconstruction of a CT image of the examination region from the measured values lying within the reconstruction window.

* * * * *